(12) United States Patent
Steiner et al.

(10) Patent No.: US 12,115,247 B2
(45) Date of Patent: Oct. 15, 2024

(54) STRUCTURED ORODISPERSIBLE FILMS

(71) Applicant: LTS LOHMANN THERAPIE-SYSTEME AG, Andernach (DE)

(72) Inventors: Denise Steiner, Braunschweig (DE); Arno Kwade, Wendeburg (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 197 days.

(21) Appl. No.: 16/486,447

(22) PCT Filed: Feb. 16, 2018

(86) PCT No.: PCT/EP2018/053920
§ 371 (c)(1),
(2) Date: Aug. 15, 2019

(87) PCT Pub. No.: WO2018/149983
PCT Pub. Date: Aug. 23, 2018

(65) Prior Publication Data
US 2020/0108011 A1    Apr. 9, 2020

(30) Foreign Application Priority Data

Feb. 17, 2017 (DE) ......................... 102017103346.7

(51) Int. Cl.
| | | |
|---|---|---|
| A61K 9/00 | (2006.01) | |
| A61K 9/70 | (2006.01) | |
| A61K 47/32 | (2006.01) | |
| A61K 47/38 | (2006.01) | |

(52) U.S. Cl.
CPC .............. *A61K 9/0056* (2013.01); *A61K 9/70* (2013.01); *A61K 47/32* (2013.01); *A61K 47/38* (2013.01)

(58) Field of Classification Search
CPC ........ A61K 9/0056; A61K 9/70; A61K 47/32; A61K 47/38
See application file for complete search history.

(56) References Cited

U.S. PATENT DOCUMENTS

| | | | | |
|---|---|---|---|---|
| 6,419,903 | B1 * | 7/2002 | Xu ....................... | A61K 8/0208 424/435 |
| 7,201,922 | B2 | 4/2007 | Serpelloni | |
| 2001/0006677 | A1 * | 7/2001 | McGinity ............ | A61K 9/0007 424/435 |
| 2005/0184427 | A1 * | 8/2005 | Yang .................... | A61K 9/7015 264/175 |
| 2007/0281975 | A1 * | 12/2007 | Mugrage ................. | A61P 3/06 514/327 |
| 2008/0003267 | A1 * | 1/2008 | Spencer ................. | A61K 9/006 514/474 |
| 2014/0120150 | A1 * | 5/2014 | McDonald, III ....... | A61K 9/006 424/78.3 |
| 2014/0377328 | A1 * | 12/2014 | Ishise .................. | A61K 31/445 514/327 |

FOREIGN PATENT DOCUMENTS

| | | | | |
|---|---|---|---|---|
| EP | 2732813 | A1 | 5/2014 | |
| EP | 2046264 | B1 | 8/2014 | |
| JP | 6336767 | A | 12/1994 | |
| JP | 2000350555 | A * | 12/2000 | |
| JP | 2004043450 | A * | 2/2004 | ............. A61K 47/26 |
| JP | 2010132653 | A | 6/2010 | |
| JP | 2014020913 | A * | 2/2014 | |
| RU | 2317812 | C2 | 2/2008 | |
| WO | 2003011248 | A1 | 2/2003 | |
| WO | 2003011259 | A1 | 2/2003 | |
| WO | 2006031209 | A1 | 3/2006 | |
| WO | 2007009800 | A2 | 1/2007 | |
| WO | 2007009801 | A2 | 1/2007 | |
| WO | WO-2009110009 | A2 * | 9/2009 | ........... A61K 31/433 |
| WO | 2013023775 | A1 | 2/2013 | |

(Continued)

OTHER PUBLICATIONS

Janßen et al. International Journal of Pharmaceutics 2013 441: 818-825 (Year: 2013).*
Bühler Kollidon® BASF (Year: 2008).*
Preis et al. International Journal of Pharmaceutics 2014 461:22-29 (Year: 2014).*
Park et al. Industrial and Engineering Chemistry Research 1998 37(11):4408-4417 (Year: 1998).*
www.fao.org/3/w6355e/w6355e01.htm (Year: 1997).*
Avicel® PH-105 Specification Sheet (2003 (Year: 2003).*

(Continued)

*Primary Examiner* — Melissa S Mercier
*Assistant Examiner* — Caralynne E Helm
(74) *Attorney, Agent, or Firm* — Lippes Mathias LLP

(57) ABSTRACT

Disclosed is a method for producing a porous orodispersible film, having the following steps: i) forming a suspension of a pharmaceutically acceptable solvent, a pharmaceutically acceptable matrix material, and a pharmaceutically acceptable binder, said solvent being selected such that the pharmaceutically acceptable matrix material substantially does not dissolve in it, whereas the pharmaceutically acceptable binder is dissolved in the solvent, ii) casting the suspension onto a neutral support, thereby forming a wet film, and iii) drying the wet film and obtaining a dry film. The films produced in this manner have a closed surface on the lower face whereas the upper face is porous, thereby allowing the application of a pharmaceutically active ingredient in the form of a suspension or a solution for example. This allows the active ingredient quantity to be adjusted individually to the particular application and produces a film base material which is suitable for the application of different active ingredients.

19 Claims, 2 Drawing Sheets

(56) References Cited

FOREIGN PATENT DOCUMENTS

WO           2015101639 A1     7/2015
WO     WO-2016009001 A1 *   1/2016             A61K 9/006

OTHER PUBLICATIONS

Harika et al. Archives of Pharmacy Practice 2012 3(3):202-216 (Year: 2012).*
Poloxamer Safety Reference International Journal of Toxicology 2008 27(Suppl. 2):93-128 (Year: 2008).*
Pharmacoat® reference (Year: 2004).*
International Search Report for PCT/EP2018/053920, Mailed Apr. 6, 2018, 6 pages.
Office Action for Chinese Application No. 201880011906.X, dated Oct. 8, 2022, 7 pages.
"Drug-printing by flexographic printing technology-A new manufacturing process for orodispersible films", (International Journal of Pharmaceutics, vol. 441, pp. 818-825, Dec. 21, 2012.

* cited by examiner upper face lower face

Binder content in relation to the total polymer concentration [-]

STRUCTURED ORODISPERSIBLE FILMS

The present invention relates to structured orodispersible films which have a closed surface on their lower face and which are porous on their upper face so that they can be loaded with an active ingredient. The present invention also relates to methods for producing such orodispersible films and the use of orodispersible films loaded with active ingredients as medicament.

PRIOR ART

Peroral administration of pharmaceutical substances is still one of the most common administration methods for medicaments. Traditional peroral administration forms are, for example, tablets or capsules, which are used as carrier systems for the oral administration of pharmaceutical substances.

Tablets or capsules are generally swallowed, which requires the patient to have a liquid available, with which the patient can take this administration form. Sometimes, however, in elderly patients or children, there are swallowing difficulties, and therefore these patients may refuse to take tablets or capsules or may take them only reluctantly. It is additionally possible that tablets and capsules might be held in the mouth by the patient for a longer period of time and then spat out. This then results frequently in poor compliance, which has an adverse effect on the progression of healing or the success of the therapy.

In order to address the described problems pharmaceutical administration forms have been developed in recent years, such as especially granular materials or oral films, which can be taken without accompanying liquid and which break down quickly in the oral cavity. Oral films are characterised especially in that they have a low layer thickness and a large surface and dissolve in the mouth in the shortest possible time (i.e. in most cases 30 seconds or less). They can be taken anytime, anywhere depending on the needs of the patient, also discreetly. There is no need for any liquid to be administered at the same time since the saliva in the oral cavity is sufficient to dissolve the film and release the active ingredient.

Oral films that contain pharmaceutical and non-pharmaceutical active ingredients and methods for their production are described, inter alia, in WO 2007/009800, WO 2007/009801 and WO 03/011259.

The focus in the pharmaceutical industry and research sector has been shifting increasingly for some years now toward the continuous tailoring and development of dosage forms in accordance with the individual needs of the patients. Thus, it should be possible in the future, with personalised medicinal products, to tailor active ingredient doses directly to the age, gender, and physical build of the patient. In order to be able to implement such a tailoring cost-effectively, new requirements are placed on the dosage forms established hitherto.

For example, carrier substances free from active ingredient(s) have been developed which in a later process step can be loaded directly for the patient in pharmacies or hospitals with doses of one or more pharmaceutical active ingredients. One of these new and forward-looking developments in recent years was constituted by research in the field of orodispersible films. These adhere directly upon contact with the mucous membranes and therefore can no longer be spat out by small children or elderly patients. In addition, they facilitate the administration of pharmaceutical active ingredients for patients who have difficulty swallowing. The active ingredients can then be absorbed into the body via the mucous membranes or, if swallowed, via the intestine.

An example of an orodispersible film that is supposedly suitable for application within the scope of a personalised medicinal product is described in WO 2013/023775 A1. The described films have a two-layer structure with a base layer, which contains a film-forming substance, and an upper layer, which contains a further film-forming substance and an active ingredient. The upper layer can be applied to the base layer by being printed on in a number of layers, whereby a loading with up to 1.12 mg per 6 cm$^2$ film surface could be achieved.

A significant disadvantage of this film and other previously known orodispersible films, however, lies in the fact that until now they could only absorb small active ingredient quantities. As a result, this dosage form has been limited hitherto to high-potency active ingredients.

Against this background there is a need for an application form for active ingredients which can absorb higher active ingredient quantities, but with which on the other hand the advantages of orodispersible films in respect of the simplicity of their use are provided. The present invention addresses this need.

DISCLOSURE OF THE INVENTION

Figure 1:
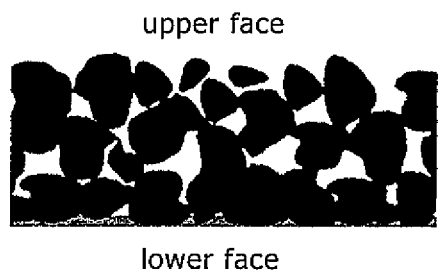
FIG. 1 is schematic illustration of the orodispersible film.

The above-described problem is addressed by orodispersible films which have an inhomogeneous porosity over their cross-section. Especially the films described here have an especially high porosity on one of their surfaces (i.e. their upper face), which enables the absorption of an active ingredient which is applied from this side to the film, whereas on the side facing away from this side (i.e. their lower face) they have a closed surface. A structure of this kind is schematically shown in FIG. 1. Surprisingly, it has been found within the scope of tests performed by the inventors that such films can be easily produced by a method as described in claim 1.

Consequently, a first aspect of the present invention relates to a method for producing a porous orodispersible film, comprising the following steps:

i) forming a suspension of a pharmaceutically acceptable solvent, a pharmaceutically acceptable matrix material, and a pharmaceutically acceptable binder, said solvent being selected such that the pharmaceutically acceptable matrix material substantially does not dissolve in it, whereas the pharmaceutically acceptable binder is dissolved in the solvent, ii) casting the suspension onto a neutral support, thereby forming a wet film, and iii) drying the wet film and obtaining a dry film.

As used herein, the term "orodispersible film" means a thin film or a thin sheet of any shape, including rectangular, square or other desired shapes, which disintegrate when they for example are moistened as a result of coming into contact with the oral mucosa of the patient or when taken orally, for example by being placed on the tongue or administered sub-lingually. The thickness and size of the orodispersible films as described herein can be adjusted to the oral cavity of the user and equally also to the desired dissolution time.

The specification that the pharmaceutically acceptable matrix material should "substantially not dissolve" in the solvent should be interpreted insofar as the solubility of the pharmaceutically acceptable matrix material in the solvent should be not more than 1 g/L, preferably not more than 0.5 g/L, and especially preferably not more than 0.1 g/L, determined in each case at ambient temperature (23° C.). With regard to the solubility it should be noted here that no more than the specified quantity of the pharmaceutically acceptable matrix material should be dissolved in the solvent at the time at which the suspension is applied to the neutral support. The pharmaceutically acceptable matrix material consequently can also be a material that dissolves only very slowly in the solvent when the application to the neutral support is performed at a time at which the specified quantity of pharmaceutically acceptable matrix material has dissolved maximally in the solvent. The above details regarding solubility, however, preferably relate to the solubility of the pharmaceutically acceptable matrix material in the solvent under conditions of equilibrium.

The provision that the pharmaceutically acceptable binder "dissolves" in the solvent shall be understood within the scope of the present invention to mean that the pharmaceutically acceptable binder shall have a solubility in the solvent of at least 10 g/l, preferably at least 50 g/l, and most preferably at least 100 g/l.

Within the scope of the present invention a "neutral support" means a support which does not in any way interact with the applied suspension. The neutral support is preferably such that the dry film obtained once the wet film has been dried can be detached easily from the neutral support, without the film tearing or breaking.

Within the scope of the drying of the wet film, described in step iii), so as to obtain a dry film it is possible in principle to feed the heat from below or from above. The expressions "from below" and "from above" mean that the heat source is positioned above or below the film.

In an especially preferred embodiment the heat in step iii) is fed from below, expediently via the neutral support. This can be implemented on the one hand in that the heat source is positioned beneath the neutral support, however it is also possible that a material which absorbs heat especially well is positioned beneath the neutral support and that the heat from the original heat source is transferred to this material. A suitable material for such a heat transfer is, for example, a metal or ceramic substrate, which is positioned directly beneath the neutral support.

As mentioned above, a key advantage of the orodispersible film obtainable by the method described above lies in the fact that it can be "loaded" with an active ingredient subsequently. In other words, an active ingredient applied subsequently, for example as a solution or suspension, to the porous orodispersible film is incorporated into the pores of the orodispersible film, such that a uniform film loaded with the active ingredient is formed. This film, on average, does not have a uniform active ingredient concentration, since the active ingredient concentration on the upper face, where the film material is more porous, is naturally higher than on the lower face, where the film is more solid, however there is no conventional two-layer structure provided, in which the active ingredient is present in one layer only at the surface of the orodispersible film.

Consequently a preferred embodiment of the above-described method, after step iii), comprises a step in which the dry film obtained there is subjected to at least one step iv) of applying a suspension or solution of a pharmaceutically active ingredient in a pharmaceutically acceptable solvent to the dry film and drying the film. As a result of this approach an orodispersible dry film is obtained, the pores of which are filled at least proportionately with the pharmaceutical active ingredient.

In some cases it may be expedient to provide the film thus obtained with a protective layer. In one embodiment of the above-described method it may therefore be expedient if the film obtained from iv) is subjected to a step v) of applying a suspension or solution of a pharmaceutically acceptable binder in a pharmaceutically acceptable solvent to the dry film obtained from step iv). As a result of this approach an orodispersible dry film is obtained, the pores of which are filled at least proportionately with the pharmaceutical active ingredient and which is coated by a protective layer of the binder.

The above-mentioned pharmaceutically acceptable solvent can be, in principle, any pharmaceutically acceptable solvent known in the prior art. Especially alcohols, comprising mono- and polyalcohols (for example glycols), esters, ketones and mixtures thereof are conceivable solvents. Water is also possible as a constituent of the pharmaceutically acceptable solvent, the proportion of which in the solvent, however, should be limited to a minimum, since the orodispersible film should dissolve upon contact with liquid in the mouth. The use of substantial proportions of water in combination with the matrix material can therefore impair the formation of the porous surface structure of the orodispersible film, and thus the proportion of water should be limited to a maximum of 20 vol. %, preferably a maximum of 10 vol. %, and especially preferably a maximum of 5 vol. %, in relation to the total quantity of solvent.

Especially short-chain alcohols with 1 to 6 carbon atoms, especially 2, 3 or 4 carbon atoms, such as methanol, ethanol and propanol, including 1-propanol and 2-propanol, are suitable as alcohols. Suitable polyalcohols include, amongst others, ethylene glycol and propylene glycol. An especially preferred alcohol as pharmaceutically acceptable solvent is ethanol. A suitable ester solvent is ethyl acetate, for example. A suitable pharmaceutically acceptable ketone solvent is acetone. Mixtures of the aforementioned solvents can also be used.

Both synthetic polymers and natural polymers, such as especially polysaccharides in modified or non-modified form, can be considered as suitable pharmaceutically acceptable matrix materials. For example, polyvinyl alcohol, polyethylene glycol, cross-linked polyvinyl pyrrolidone and copolymers thereof can be cited as preferred synthetic polymers. Especially preferred polysaccharides include cellulose and derivatives thereof, such as especially hydroxyalkyl methyl cellulose and preferably hydroxyethyl methyl cellulose and/or hydroxypropyl methyl cellulose, starches, starch derivatives, modified starches, such as maltodextrin, di- and oligosaccharides (with 2 to 10 sugar units) and glycomannans. A further suitable pharmaceutically acceptable matrix material is alginate.

Hydroxypropyl methyl cellulose, especially a hydroxypropyl methyl cellulose with a hydroxypropyl proportion of from 5% to 15%, a methyl proportion of from 25% to 35%, and a viscosity of approximately 6 MPa·s as 2% aqueous solution at 20° C. can be cited as an especially suitable pharmaceutically acceptable matrix material. The quantities of hydroxypropyl and methyl relate to the relative quantities in relation to the monomer units of the polymer. Thus, in a polymer that contains 10% hydroxypropyl, 10% or 1 in 10 monomer units of the polymer contain a hydroxypropyl substituent.

Specific examples of suitable pharmaceutically acceptable matrix materials are different commercially obtainable hydroxypropyl methyl cellulose products which are obtainable under the trade names Pharmacoat 606 (hydroxypropyl methyl cellulose, viscosity 6 MPa·s, Shin-Etsu Chemical Co. Ltd., Japan), Methocell E3 and Methocell E5 (hydroxypropyl methyl cellulose, viscosity 3 MPa·s and 5 MPa·s respectively, Dow Chemical Company, USA).

A matrix material that likewise is especially suitable is lactose.

The pharmaceutically acceptable matrix material can also comprise a mixture of a plurality of the above-mentioned specific matrix materials, for example of a mixture of hydroxypropyl methyl cellulose and lactose.

The particle size of the pharmaceutical matrix material assumes some significance within the scope of the present invention, since the particle size to a certain extent has an effect on the type and size of the pores that form following the drying of the wet film. Suitable mean particle sizes for the pharmaceutically acceptable matrix material can lie within a range of from 10 to 200 µm, especially 50 to 150 µm, preferably 70 to 130 µm, and especially preferably 80 to 120 µm.

The particle size in this case denotes the volumetrically weighted particle size and is determined by means of the laser diffraction method.

With regard to the pharmaceutically acceptable binder, synthetic polymers, for example in the form of polyvinyl pyrrolidone, or polysaccharides, preferably in the form of cellulose derivatives, and especially hydroxypropyl cellulose, can be cited within the scope of the present invention. Hydroxypropyl cellulose can be cited as a preferred binder and is obtainable, inter alia, in the form of HPC from Sigma Aldrich.

Especially preferred matrix material/binder combinations are for example hydroxypropyl methyl cellulose (matrix)/hydroxypropyl cellulose (binder) or lactose (matrix)/hydroxypropyl cellulose (binder).

The quantity of the pharmaceutically acceptable binder with respect to the total quantity of pharmaceutically acceptable matrix material and binder assumes a certain significance within the scope of the present invention. It has been found that for very low binder contents it was not possible to obtain a closed lower face of the film, which led to a significantly reduced strength of the film. By contrast, in the case of excessively high binder contents a much denser film formed, which had a lower porosity, which significantly reduced the ability of the film to absorb a subsequently applied pharmaceutical active ingredient. A suitable proportion of pharmaceutically acceptable binder in the total quantity of pharmaceutically acceptable matrix material and binder can be specified as a range of from 0.1 to 0.5, especially 0.2 to 0.4, preferably 0.25 to 0.33, and especially preferably 0.27 to 0.31.

The solvent quantity within the scope of the above-described method also assumes a certain significance. It was found that, with an excessively low solvent quantity, the suspension had an excessively high viscosity, which led to films of non-uniform thickness and an increased risk of blockages of the nozzle used to apply the suspension. On the other hand an excessively high proportion of solvent is unfavourable, since it has to be removed from the film product within the scope of the drying process, which has a negative impact from an energy viewpoint. A suitable proportion of the solvent, in relation to the total weight of the suspension, can be a proportion in the range of from 0.4 to 0.9, especially 0.68 to 0.8, preferably 0.7 to 0.76, and especially preferably from 0.71 to 0.75.

The pharmaceutical active ingredient can be, in principle, any pharmaceutical active ingredient suitable for oral administration. Especially the pharmaceutical active ingredient is suitable for oral applications. Examples of suitable pharmaceutical active ingredients are antiallergics, antiarrhythmics, antibiotics, antidiabetics, antiepileptics, antihistamines, antitussives, cardiotonic agents, diuretics, blood-pressure-lowering agents, anaesthetics, nerve muscle blockers and sexual hormones, such as vasopressors. Specific examples are acetaminophen, adrenaline, alprazolam, amlodipine besylate, anastrozole, apomorphine, aripiprazole, atorvastatin calcium, baclofen, benzocaine, benzocaine/menthol, benzydamine, buprenorphine, buprenorphine/naloxone, buprenorphine/naloxone/cetirizine, cetirizine, especially in the form of cetirizine HCl, cannabinoids, chlorpheniramine, clomipramine, DBP-166, dexamethasone, dextromethorphan, dextromethorphan/phenylephrine, diclofenac, diphenhydramine, especially in the form of diphenhydramine hydrochloride, diphenhydramine/phenylephrine, donepezil, especially in the form of donepezil hydrochloride, dronabinol, epinephrine, escitalopram, famotidine, fentanyl, glimepiride, GLP-1 peptides, granisetron, insulin, insulin nanoparticles, insulin/GLP-1 nanoparticles, INT-0020, INT-0022, INT-0023, INT-0025, INT-0030, INT-0036, INT-0031/2012, ketoprofen, ketotifen fumarate, caffeine, levocetirizine, loperamide, loratadine, meclizine hydrochloride, methylphenidate, midazolam maleate, mirodenafil hydrochloride, montelukast, especially in the form of montelukast sodium, multimeric-001, naloxone, nicotine, nitroglycerin, olanzapine, olopatadine hydrochloride, ondansetron, especially in the form of ondansetron hydrochloride, oxybutynine, pectin, pectin/menthol, pectin/ascorbic acid, PediaSUNAT (artesunate and amodiaquine), piroxicam, phenylephrine, especially in the form of phenylephrine hydrobromide or hydrochloride, prednisolone, pseudoephedrine, risperidon, rivastigmine, rizatriptan, especially in the form of rizatriptan benzoate, selegiline, senna glycosides, sildenafil citrate, simethicone, SPO-1202, SPO-1201, SPO-1113, SPO-1108 SPO-111, sumatriptan, tadalafil, testosterone, triamcinolone azetonide, triptan, tropicamide, voglibose, zolmitriptan, zolpidem, especially in the form of zolpidem tartrate. Furthermore, the pharmaceutical active ingredient can be suitable for oral hygiene, such as menthol. The pharmaceutical active ingredient can also be a mixture of different active ingredients.

The orodispersible film can also be used as a support for a vaccine, wherein the pharmaceutical active ingredient in this case is present in the form of a vaccine, for example as a rotavirus vaccine.

The quantity of the pharmaceutical active ingredient in the orodispersible film lies preferably in the range of from 0.001 to 10 mg/cm$^2$, especially 0.01 to 10 mg/cm$^2$, more preferably 2 to 8 mg/cm$^2$ and most preferably 3 to 7 mg/cm$^2$.

Alternatively to a pharmaceutical active ingredient, the orodispersible film according to the invention can also be loaded with one or more vitamins, for example in the form of biotin, vitamin B6, vitamin B12, vitamin D3, vitamin E and vitamin C, electrolytes such as sodium or potassium salts and mixtures thereof, stimulants, such as caffeine, and plant extracts such as guarana extract, ginseng extract or cranberry extract, or mixtures thereof. Consequently, a further embodiment of the present invention relates to a method as described above with a step iv) of applying a suspension or solution of a pharmaceutically active ingredient, in which, however, instead of the pharmaceutical active ingredient, a suspension or solution of one or more selected from vitamins, electrolytes, stimulants and plant extracts is/are applied to the film.

The orodispersible film, after the casting as a wet film, preferably has a wet-layer thickness in the range of from 400 µm to 1500 µm and preferably in the range of from 800 to 1200 µm. A range of from 150 µm to 600 µm and especially 290 to 350 µm can be cited as an especially suitable layer thickness of the dry film.

The film furthermore expediently has a theoretical porosity in the range of from 0.4 to 0.7, especially 0.52 to 0.7, preferably in the range of from 0.55 to 0.68 and especially preferably in the range of from 0.58 to 0.66. The theoretical porosity E is calculated in this case in accordance with the equation $$e = \frac{V_{SoFT} -' - \frac{(m_{soFr})}{P_{soFr}}}{V_{SoFT}}$$

wherein $V_{SOFT}$ specifies the volume of the film, $m_{SOFT}$ specifies the mass of the film, and $\rho_{SOFT}$ specifies the mean density of the film. As explained above, the porosity is not uniform over the cross-section of the film according to the invention. The porosity specified here therefore constitutes the mean value of the porosity over the cross-section of the film.

Within the scope of step iii) or in the context of the above-described steps iv) and v), the drying is performed expediently in a temperature range suitable for the evaporation of the solvent used. The temperature of the drying is selected here expediently, at least in the starting stage of the drying process, such that it lies in the region of or slightly below the boiling point of the pharmaceutically acceptable solvent, so as on the one hand to attain the quickest evaporation possible of the solvent, but on the other hand to avoid a boiling of the solvent, in which case bubbles that might be detrimental to the uniformity of the film will form. For most of the suitable pharmaceutically acceptable solvents mentioned above, a temperature range of from 40 to 80° C., preferably 45 to 70° C., and especially preferably 48 to 60° C. can be cited as suitable.

Within the scope of the method described above for producing an orodispersible film, it is possible to add a pharmaceutical active ingredient already during the formation of the suspension in step i), which pharmaceutical active ingredient is then incorporated directly in the film within the scope of the casting and drying in steps ii) and iii). In this case it is possible via step iv), explained above, to introduce additionally a further active ingredient, which can be different from the active ingredient used in step i), into the porous orodispersible film. For example, with use of the same active ingredient, the quantity of the active ingredient, starting from a base loading, can be adjusted individually to the needs of the patient. If the active ingredient used in step iv) is different from the active ingredient used in step i), there is likewise flexibility in respect of this second active ingredient, which can be used to tailor the active ingredient quantity to the patient in question.

In order to stabilise the pharmaceutical active ingredient in step iv), it can be expedient if a stabiliser for the active ingredient is additionally added to the suspension or solution of the active ingredient in a pharmaceutically acceptable solvent. This stabiliser, in an embodiment of the above-described method, is the pharmaceutically acceptable binder used in step i). An especially suitable material for the stabiliser is consequently hydroxypropyl cellulose. Alternatively or additionally, synthetic polymer stabilisers can be used. Suitable synthetic polymer stabilisers are for example vinyl pyrrolidone polymers and copolymers, especially vinyl pyrrolidone-vinyl acetate copolymers, as are sold for example under the trade name Kollidon® VA 64 by BASF, DE.

Besides the above-explained constituents, further ingredients can be added for the formation of the suspension in step i), but also within the scope of the application of a suspension or solution of a pharmaceutical active ingredient in step iv). Examples of such ingredients are, for example, hydrophilising agents, such as polyoxyethylene lauryl ethers, for example commercially obtainable as Brij35 (for example Merck KGaA, Germany), flavourings, odorants, aromatic substances and/or colouring agents, such as dyes and/or pigments.

A further aspect of the above-explained invention relates to an orodispersible dry film which is obtainable by a method as described above. This dry film is characterised in respect of its surface condition in that it is porous on one side, which allows the introduction of a suspension or solution, whereas on the other side of the film a closed surface is provided, to which such a suspension or solution can be merely applied, but does not penetrate the film material. This structure of the film is attained by the above-explained method.

The film preferably contains pores from a distance of 20 µm from the lower face, preferably from a distance of 10 µm from the lower face, or, if the film is one in which the pores are filled at feast proportionately with pharmaceutical active ingredient, it contains traceable quantities of active ingredient.

One aspect of the present invention furthermore relates to an orodispersible dry film, the pores of which are filled at least proportionately with a pharmaceutical active ingredient and which is producible in a method which includes a step iv) as described above. Corresponding orodispersible films can be used especially as a medicament.

With regard to preferred embodiments of the last-mentioned aspects, reference can be made to the explanations above.

A further aspect of the present invention relates lastly to an orodispersible dry film with a dry-layer thickness in the range of from 100 to 600 µm, a theoretical porosity in the range of from 0.4 to 0.7, and a tensile strength in the range of from 0.4 to 4 $Nmm^{-2}$, which film comprises a pharmaceutically acceptable matrix material and a pharmaceutically acceptable binder as constituents. With regard to preferred embodiments of the dry-layer thickness and the theoretical porosity, as well as the binder and the matrix material, reference can be made to the explanations above. The film preferably has a structure such that it has a closed surface on one side of the film and is porous on the other side, such that a liquid which is applied to the closed surface remains on said closed surface, whereas a liquid which is applied to the porous side of the film can penetrate the film. In addition, the orodispersible dry film preferably has a disintegration time in the range of from 5 to 250 seconds when this is determined as described in the "Examples" section.

Preferred disintegration times for these films can be cited as a period of time of from 10 to 120 seconds, and especially 20 to 60 seconds. Alternatively or additionally, a tensile strength of from 0.6 to 2.5 $Nmm^{-2}$ is preferred, and a tensile strength of from 0.8 to 1.8 $Nmm^{-2}$ is especially preferred.

The pores of the film can be filled with a pharmaceutical active ingredient, whereby a theoretical porosity can be provided which lies below the above-mentioned value. In this case the orodispersible dry film also comprises a pharmaceutical active ingredient in addition to the pharmaceutically acceptable matrix material and the pharmaceutically acceptable binder.

The present invention will be explained hereinafter on the basis of some illustrative examples, however these are not to be considered to limit the scope of the application in any way.

EXAMPLES

Example 1

The following tests were performed on the basis of suspensions having different matrix/binder ratios. The suspensions used for this purpose contained ethanol as solvent, HMPC (Pharmacoat 606) as matrix material and HPC (Sigma Aldrich) as binder. The suspension was produced by dissolving HPC in ethanol and subsequently adding the matrix material. The suspension thus obtained was degassed for 16 hours and was then applied to a PET film using an automatic ZAA 2300 film applicator (Zehntner, Switzerland). The application rate was 10 mm s$^{-1}$ and the distance from the substrate was 1000 µm. The films were dried at 50° C. for 30 min in a furnace and were then detached from the substrate.

In the suspensions used for production of the films the ethanol content was $c_{EtOH}$=0.735. The proportion of the binder, in relation to the total quantity of matrix material and binder ($c_{HPC}$), was varied in the range of from 0.25 to 0.33. For each of the films thus obtained the film thickness, the disintegration time, and the film strength were determined on the basis of the following methods.

Thickness:

The dry-layer thickness was determined using a digital dial indicator with a circular contact area on the sample (diameter approximately 3 mm) with an accuracy of 0.001 mm from Mitutoya Deutschland GmbH as the mean value of 10 independent measurements.

Disintegration Time:

The disintegration time was determined using the SFaB (slide frame and ball) method, which is described by Steiner in *International Journal of Pharmaceutics*, vol. 511, 2016, p. 804-813. To this end, films with the dimensions 3×4 cm were clamped in a frame so that the open pores were at the upper side of the assembly. The measurement was started when the ball (stainless steel, $m_{Ball}$=4 g, d=10 mm) had been placed on the first droplet of 0.9 ml distilled water (T=37° C.). Once the measurement had started the rest of the water was applied to the film surface. The disintegration time was defined as the time taken by the water to break down the orodispersible film until the ball fell downwards 200 mm, through the film, onto the base of the assembly. For improved comparability, the specific disintegration time was calculated as the quotient of the measured disintegration time and the film thickness.

Tensile Strength:

The tensile strength was determined using a material-testing machine (8136/20N, Zwick GmbH & Co. KG) with test strips measuring 5×35 mm. The test strips were clamped between the two grippers and pulled apart at a rate of 5 mm/min. The maximum force, $F_{max}$, until the orodispersible film tore was recorded and specified as the mechanical strength of the film. The tensile strength of the film was given as the quotient of $F_{max}$ and cross-sectional area.

Figure 2:
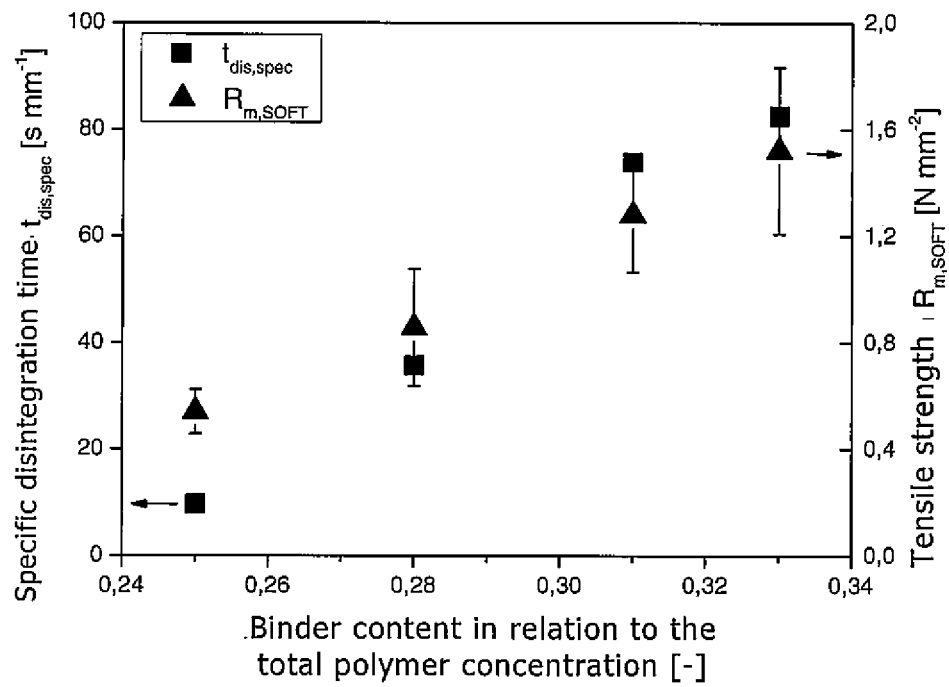
FIG. 2 is a graph displaying the disintegration time and tensile strength for Example 1.

The results of the thickness determinations are shown in Table 1 below. The results of the disintegration time and the tensile strength are shown in FIG. 2.

TABLE 1

| $c_{HPC}$ | Film thickness |
|---|---|
| 0.28 | 410 µm |
| 0.31 | 280 µm |
| 0.33 | 210 µm |

It was found that the thickness decreases with increasing binder concentration, such that the films as a whole have a lower porosity. This reduces the capacity to absorb an active ingredient. On the other hand it was observed that with low binder contents it was no longer ensured that a closed surface was obtained on the lower face.

It can additionally be inferred from FIG. 2 that the tensile strength of the films, but also the disintegration time thereof increased with increasing binder contents.

Example 2: Loading of Orodispersible Films with a Model Active Ingredient

Figure 3:
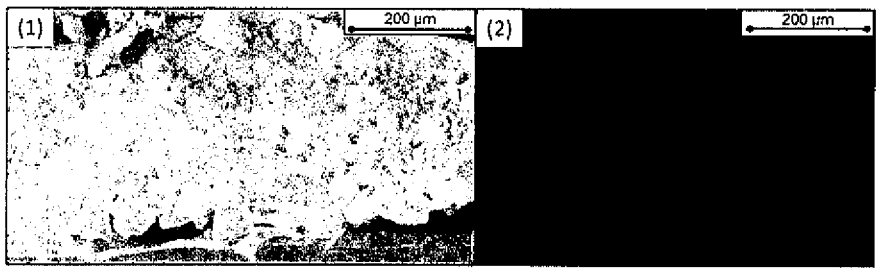
FIG. 3 is to SEM/EDX distribution of the aluminum oxide for Example 2.

In order to be able to determine the distribution of a model active ingredient in the orodispersible films according to the invention, the loading of the films was examined with regard to a clear detection with an aluminium oxide suspension ($x_{50}$=100 nm, solvent=ethanol). The distribution of the aluminium oxide in the film was then determined by SEM/EDX (element tracking) (see FIG. 3). These tests were able to show that the incorporation of the particles in the film pores was possible and that the suspensions penetrated the orodispersible film as far as the closed lower face. It was also possible to show that the porous matrix film did not dissolve during the loading.

Example 3: Variation of the Coating Cycles and Particle Concentration

For these tests an anthraquinone suspension ($x_{50}$=400 nm) was used. These contained, in addition to the anthraquinone, also HPC as stabiliser in a concentration of $c_{HPC}$=0.25 (in relation to the total quantity of anthraquinone in the suspension). The concentration of the suspension was varied in a range of from 0.05 to 0.2, and the suspension was applied between one and five times to the film. The suspension was applied to the film surface via an application nozzle with a volume of 25 µm/min at a rate of 220 mm/min. The film used for the tests was a film with $c_{HPC}$=0.28, as described in Example 1.

Figure 4:
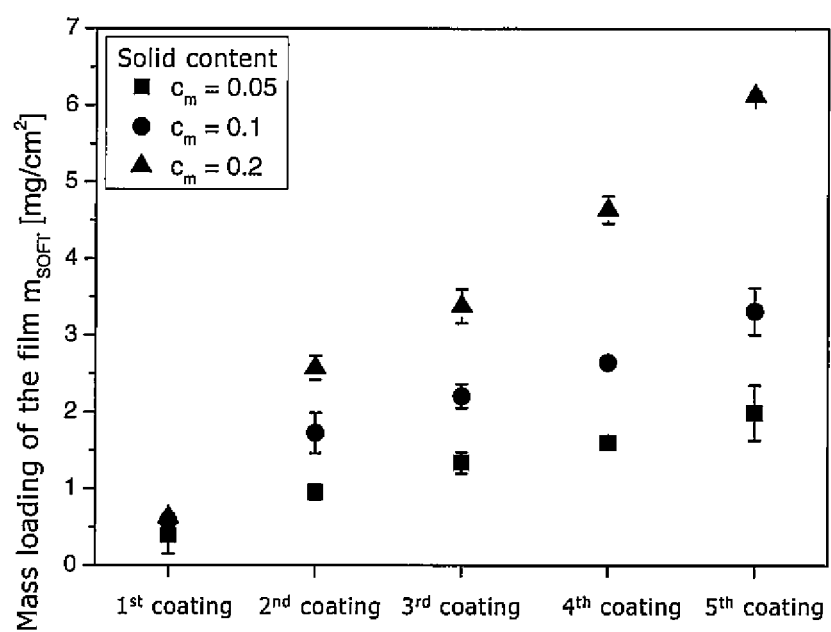
FIG. 4 is a graph displaying the anthraquinone loading for Example 3.

The loading with anthraquinone was determined for each of the obtained films. The results of these tests are shown in FIG. 4.

The tests showed that the highest loading of 6.1 mg/cm$^2$ with an anthraquinone concentration of 0.2 could be realised in five coating cycles. This corresponds to an anthraquinone loading of 4.9 mg/cm$^2$. Under consideration of the standard variable of an orodispersible film of 6 cm$^2$, this thus gives a maximum active ingredient loading of approximately 30 mg.

The invention claimed is:

1. A method for producing an orodispersible film, comprising the following steps:
   i) forming a suspension of a pharmaceutically acceptable solvent, a pharmaceutically acceptable matrix material, and a pharmaceutically acceptable binder, said solvent being selected such that the solubility of the pharmaceutically acceptable matrix in the solvent is not more than 1 g/L, whereas the pharmaceutically acceptable binder is dissolved in the solvent, wherein the proportion of pharmaceutically acceptable binder in the total quantity of pharmaceutically acceptable matrix material and binder lies in the range of from 0.2 to 0.5, and wherein the solvent has a water content of maximum 20 vol. %, in relation to the total quantity of solvent,
   ii) casting the suspension onto a neutral support, thereby forming a wet film,
   iii) drying the wet film and obtaining a porous dry film, and iii)
   iv) applying a suspension or solution of a pharmaceutically active ingredient in a pharmaceutically acceptable solvent to the porous dry film and drying the film, an orodispersible dry film being obtained, the pores of which are filled at least partially with the pharmaceutically active ingredient.

2. The method according to claim 1, characterised in that within the scope of step iii) heat is fed from below via the neutral support.

3. The method according to claim 1, characterised in that within the scope of step iii) heat is fed from above.

4. The method according to claim 1, characterised in that the film obtained from step iv) is subjected to a step v) of applying a suspension or solution of a pharmaceutically acceptable binder in a pharmaceutically acceptable solvent having a water content of maximum 20 vol. %, in relation to the total quantity of solvent, to the dry film obtained from step iv), an orodispersible dry film being obtained, the pores of which are filled at least proportionately with the pharmaceutically active ingredient and which is coated by a protective layer of the binder.

5. The method according to claim 1, characterised in that an alcohol, optionally in the form of ethanol, an ester or mixtures thereof, is used as the pharmaceutically acceptable solvent.

6. The method according to claim 1, characterised in that a polysaccharide, optionally in the form of cellulose or a cellulose derivative and optionally in the form of hydroxypropyl methyl cellulose, is used as the pharmaceutically acceptable matrix material.

7. The method according to claim 1, characterised in that the pharmaceutically acceptable matrix material has a mean particle size in the range of from 10 to 200 µm, or 50 to 150 µm, or 70 to 130 µm, or in the range of from 80 to 120 µm.

8. The method according to claim 1, characterised in that a synthetic polymer, optionally in the form of polyvinyl pyrrolidone, or a polysaccharide, optionally in the form of a cellulose derivative, optionally in the form of hydroxypropyl cellulose, is used as pharmaceutically acceptable binder.

9. The method according to claim 1, characterised in that the proportion of pharmaceutically acceptable binder in the total quantity of pharmaceutically acceptable matrix material and binder lies in the range of from 0.2 to 0.4, or from 0.25 to 0.33, or from 0.27 to 0.31.

10. The method according to claim 1, characterised in that the proportion of solvent, in relation to the total weight of the suspension in step i), lies in the range of from 0.4 to 0.9, or 0.68 to 0.8, or from 0.70 to 0.76, or from 0.71 to 0.75.

11. The method according to claim 1, characterised in that the film has a wet-layer thickness in the range of from 400 µm to 1500 µm, or in the range of from 800 µm to 1200 µm, and/or a dry-layer thickness in the range of from 150 µm to 600 µm, or in the range of from 290 to 350 µm.

12. The method according to claim 1, characterised in that the drying is performed at a temperature in the range of from 40° ° C. to 80° C., or 45° ° C. to 70° ° C. or 48° C. to 60° C.

13. The method according to claim 1, characterised in that the suspension or solution of the pharmaceutically active ingredient in a pharmaceutically acceptable solvent having a water content of maximum 20 vol. %, in relation to the total quantity of solvent, additionally contains a stabiliser for the pharmaceutically active ingredient, this being the pharmaceutically acceptable binder used in step i).

14. The method according to claim 1, characterised in that the film after drying has a pharmaceutically active ingredient loading in the range of from 0.01 to 10 mg/cm$^2$, or 2 to 8 mg/cm$^2$, or 3 to 7 mg/cm$^2$.

15. The method according to claim 1, wherein the pharmaceutically acceptable matrix material is selected from polyvinyl alcohol, polyethylene glycol, hydroxyalkyl methyl cellulose, starches, starch derivatives, modified starches, di- and oligosaccharides with 2 to 10 sugar units, glycomannans, alginate or mixtures thereof.

16. An orodispersible dry film obtainable by a method according to claim 1.

17. A method for producing a porous orodispersible film, comprising the following steps:
   i) forming a suspension of a pharmaceutically acceptable solvent, a pharmaceutically acceptable matrix material, and a pharmaceutically acceptable binder, said solvent being selected such that the solubility of the pharmaceutically acceptable matrix material in the solvent is not more than 1 g/L, whereas the pharmaceutically acceptable binder is dissolved in the solvent, wherein the proportion of pharmaceutically acceptable binder in the total quantity of pharmaceutically acceptable matrix material and binder lies in the range of from 0.1 to 0.5,
   ii) casting the suspension onto a neutral support, thereby forming a wet film, and
   iii) drying the wet film and obtaining a dry porous film, wherein the pharmaceutically acceptable matrix material is selected from polyvinyl alcohol, polyethylene glycol, hydroxyalkyl methyl cellulose, di- and oligosaccharides with 2 to 10 sugar units, glycomannans, alginate or mixtures thereof.

18. The method according to claim 17, wherein the pharmaceutically acceptable matrix material is hydroxypropyl methyl cellulose.

19. An orodispersible dry film obtainable by a method according to claim 17.

* * * * *